US010448892B2

(12) United States Patent
Tian

(10) Patent No.: US 10,448,892 B2
(45) Date of Patent: Oct. 22, 2019

(54) COMPASS-SENSOR EMBEDDED FOOTWEAR SYSTEM AND OPERATION METHOD THEREOF

(71) Applicant: Xin Tian, Niskayuna, NY (US)

(72) Inventor: Xin Tian, Niskayuna, NY (US)

(73) Assignee: Xin Tian, Niskayuna, NY (US)

( * ) Notice: Subject to any disclaimer, the term of this patent is extended or adjusted under 35 U.S.C. 154(b) by 306 days.

(21) Appl. No.: 15/283,764

(22) Filed: Oct. 3, 2016

(65) Prior Publication Data

US 2018/0070877 A1 Mar. 15, 2018

Related U.S. Application Data

(60) Provisional application No. 62/394,048, filed on Sep. 13, 2016.

(51) Int. Cl.
| | | |
|---|---|---|
| *A61B 5/00* | (2006.01) | |
| *A43B 3/00* | (2006.01) | |
| *A61B 5/103* | (2006.01) | |
| *A43B 13/00* | (2006.01) | |
| *A43B 17/00* | (2006.01) | |
| *G01C 17/02* | (2006.01) | |

(52) U.S. Cl.
CPC .......... *A61B 5/6807* (2013.01); *A43B 3/0005* (2013.01); *A43B 3/0015* (2013.01); *A43B 13/00* (2013.01); *A43B 17/00* (2013.01); *A61B 5/0024* (2013.01); *A61B 5/1038* (2013.01); *G01C 17/02* (2013.01); *A61B 2562/0247* (2013.01); *A61B 2562/04* (2013.01)

(58) Field of Classification Search
CPC . A61B 5/112; A61B 5/1121–3; A61B 5/1036; A61B 5/6807; A43B 3/0005; A43B 3/0015; A43B 13/00
See application file for complete search history.

(56) References Cited

U.S. PATENT DOCUMENTS

| | | | |
|---|---|---|---|
| 8,172,722 B2* | 5/2012 | Molyneux ............ | A43B 1/0054 482/1 |
| 8,827,815 B2* | 9/2014 | Burroughs .......... | G06F 19/3481 463/42 |
| 8,935,119 B2* | 1/2015 | Yuen ...................... | G01B 21/16 702/138 |
| 9,232,911 B2* | 1/2016 | Wilson ................. | A61B 5/1038 |
| 9,591,993 B2* | 3/2017 | Morris Bamberg ........................ A61B 5/1038 | |
| 9,743,861 B2* | 8/2017 | Giedwoyn ............ | A61B 5/112 |
| 9,763,489 B2* | 9/2017 | Amos ................... | A43B 3/0005 |
| 9,993,181 B2* | 6/2018 | Ross ...................... | A61B 5/112 |
| 10,034,622 B1* | 7/2018 | Mahmoud ............ | A61B 5/1038 |
| 10,070,680 B2* | 9/2018 | Molyneux ................ | A43B 3/00 |
| 10,188,170 B2* | 1/2019 | Bramani ................ | A43B 3/001 |
| 2011/0087445 A1* | 4/2011 | Sobolewski ......... | A43B 1/0054 702/44 |

* cited by examiner

*Primary Examiner* — Max F Hindenburg
(74) *Attorney, Agent, or Firm* — Anova Law Group, LLC

(57) ABSTRACT

A compass-sensor embedded footwear system and an operation method thereof are provided. The compass-sensor embedded footwear system includes: a footwear including: a footwear sole; two pressure sensors embedded in the footwear sole; a compass sensor configured in a fixed orientation with respect to the footwear sole; and a control-communication unit connecting to each of the two pressure sensors and compass sensor.

17 Claims, 9 Drawing Sheets

Left Footwear

Right Footwear

COMPASS-SENSOR EMBEDDED FOOTWEAR SYSTEM AND OPERATION METHOD THEREOF

CROSS-REFERENCES TO RELATED APPLICATIONS

This application claims the priority of Provisional Patent Application No. 62/394,048, filed on Sep. 13, 2016, the entire content of which is incorporated herein by reference.

FIELD OF THE DISCLOSURE

The present disclosure generally relates to the field of information technology and, more particularly, relates to a compass-sensor embedded footwear system and an operation method thereof, for providing foot and/or user directional information and foot gesture information.

BACKGROUND

Sensors may be embedded in a footwear such as shoes to measure physical activities of users, e.g., for health applications on smart phones. However, due to limited space and limited power supply available in a footwear system, it is difficult to use a minimum number of precisely selected and positioned sensors to provide the most valuable information from feet for the targeted types of applications.

The disclosed compass-sensor embedded footwear system and operation method thereof are directed to solve one or more problems set forth above and other problems in the art.

BRIEF SUMMARY OF THE DISCLOSURE

One aspect of the present disclosure provides a compass-sensor embedded footwear system. The compass-sensor embedded footwear system includes: a footwear including: a footwear sole; two pressure sensors embedded in the footwear sole; a compass sensor configured in a fixed orientation with respect to the footwear sole; and a control-communication unit connecting to each of the two pressure sensors and compass sensor.

Optionally, the footwear further includes a battery module connected to the control-communication unit, and the battery module is embedded in the footwear sole or attached to an outer surface of the footwear including the footwear sole.

Optionally, the footwear, including a footwear sole, is in a form of a shoe or a shoe insole.

Optionally, the two pressure sensors are positioned on two areas of the footwear sole, such that: when a human foot is wearing the footwear, the two areas correspond to a fore part and a heel part of the human foot.

Optionally, the compass sensor is placed, such that when the footwear sole is substantially leveled in a horizontal position, the compass sensor is in normal operation.

Optionally, each of the compass sensor and the control-communication unit is embedded in the footwear sole or attached to an outer surface of the footwear including the footwear sole.

Optionally, the pressure sensors, the compass sensor, the control-communication unit, and a battery module are together embedded in the footwear sole.

Optionally, the system further includes a power-control-communication unit attached to an outer surface of the footwear including the footwear sole. The power-control-communication unit is detachable and re-attachable to the footwear, the power-control-communication unit includes a battery module and the control-communication unit. The pressure sensors and the compass sensor are embedded in the footwear sole.

Optionally, the system further includes a power-control-communication-compass unit attached to an outer surface of the footwear including the footwear sole. The power-control-communication-compass unit is detachable and re-attachable to the footwear, and the power-control-communication-compass unit includes a battery module, the compass sensor, and the control-communication unit.

Optionally, the system further includes a pair of footwear corresponding to a pair of human feet.

One aspect of the present disclosure provides a method for using a compass-sensor embedded footwear system. The method includes: at a data sampling time, obtaining pressure measurements from pressure sensors embedded in a left footwear and a right footwear; based on the pressure measurements, determining sole area touch detection results corresponding to ground touches made by areas on each footwear sole of the left footwear and the right footwear; obtaining compass measurements from a compass sensor in each of the left and right footwear to provide an angle from a North direction of a local North-East coordinate system to a Y axis of the compass sensor's reference coordinate system; obtaining a relationship between the compass sensor's reference coordinate system and a corresponding footwear pointing direction based on the compass-sensor embedded footwear system; based on the obtained relationship and the angle from the compass measurements, evaluating the left and right foot pointing direction angles in the local North-East coordinate system; and gathering information from the pressure measurements, the sole area touch detection results, and the footwear pointing direction angles for both the left footwear and the right footwear for a joint processing of the gathered information.

Optionally, the step of the joint processing of the gathered information includes: combining the sole area touch detection results from the left footwear and the right footwear to obtain a user touch detection outcome at each data sampling time; fusing left and right footwear pointing direction angles for both the left footwear and the right footwear, with respect to the pressure measurements, to provide user directional information in the local North-East coordinate system; and determining foot gestures based on current and history information of: the user touch detection outcomes, the left and right footwear pointing direction angles, and pressure measurements from the pressure sensors.

Optionally, a pressure measurement from each pressure sensor is compared to a threshold level to determine if the corresponding sole area is in touch with the ground to provide a sole area touch detection result; the sole area touch detection results for each foot are combined to obtain foot-level touch detection results; and the foot-level touch detection results for both feet are further combined to obtain the user touch detection outcome at a data sampling time.

Optionally, the left and right footwear pointing direction angles are converted to foot direction vectors in a common local North-East coordinate system, which is further fused along with the pressure measurements to obtain the user directional information.

Optionally, the foot gestures are determined based on a transition sequence between touch detection states, in conjunction with the left foot direction vector and right foot direction vector information, the touch detection state is a set of multiple possible user touch detection outcomes, and the user touch detection outcome corresponds to a detection of none, one or multiple sole area touches to the ground.

Optionally, the foot gestures include Left foot taps, Right foot taps, one foot hops, jump and four types of foot wiggling movements.

Optionally, pressure measurements are used to provide additional feature information for foot gesture detections, which allows further differentiation among a same type of foot gestures including a differentiation of small jumps and big jumps.

Optionally, the method further includes: performing, by an external device, the joint processing of the gathered information by transmitting the information of the pressure measurements, the sole area touch detection results, and the footwear pointing direction angles for both the left footwear and the right footwear directly from the left and right footwear through wireless communication links to the external device.

Optionally, for the joint processing of the gathered information from both the left and right footwear, the compass-sensor embedded footwear system is configured to operate in a master-slave mode. One of the left and the right footwear is configured as the master, and the other footwear is configured as the slave, in the master-slave mode, the pressure measurements, the sole area touch detection results, and/or the footwear pointing direction angles from the left footwear or the right footwear are sent from the slave to the master through a wireless communication link for performing information fusion processes and foot gesture detections, and the master sends the foot directional information, fused user directional information and foot gesture detection results to an external device through another wireless communication link.

Optionally, the method further includes: repeating each step at every sampling time performed by the compass-sensor embedded footwear system.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Figure 1:
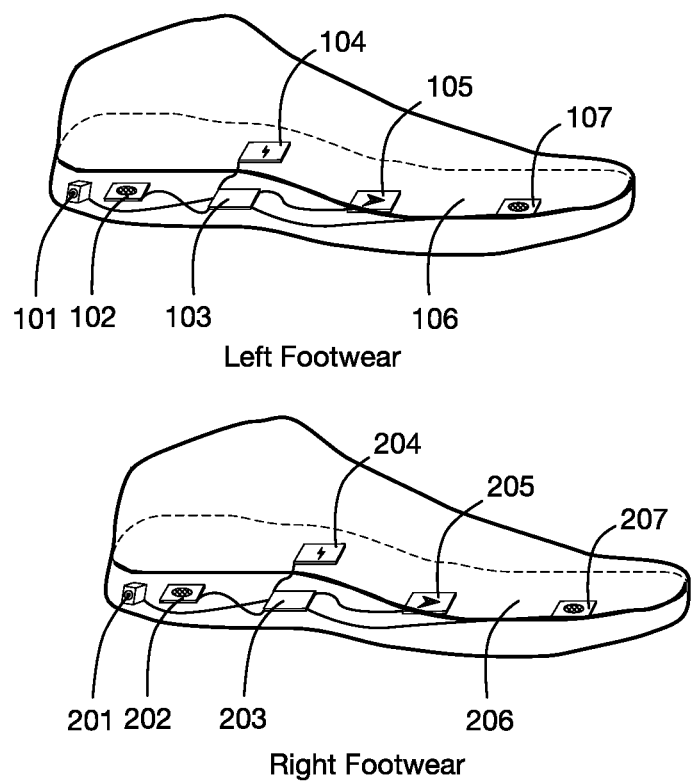
FIG. 1 illustrates an exemplary compass-sensor embedded footwear system according to various embodiments of the present disclosure.

Reference will now be made in detail to exemplary embodiments of the disclosure, which are illustrated in the accompanying drawings. Hereinafter, embodiments consistent with the disclosure will be described with reference to drawings. Wherever possible, the same reference numbers will be used throughout the drawings to refer to the same or like parts. It is apparent that the described embodiments are some but not all of the embodiments of the present disclosure. Based on the disclosed embodiment, persons of ordinary skill in the art may derive other embodiments consistent with the present disclosure, all of which are within the scope of the present disclosure.

The present disclosure provides a compass-sensor embedded footwear system and operation method thereof. An exemplary compass-sensor embedded footwear system may include a footwear and/or a pair of footwear corresponding to a pair of human feet including, e.g., a left footwear and a right footwear. Each footwear includes a compass sensor, (i.e., a sensor that is able to provide direction/direction angle measurements of the North direction in its own reference 2D coordinate system) to provide foot directional information; two pressure sensors to obtain pressure measurements at designed sole areas of the footwear, and/or a control-communication unit and a power module supporting the system operation.

In some embodiments, the footwear used in the compass-sensor embedded footwear system may include a footwear sole and footwear body. In other embodiments, the footwear used in the compass-sensor embedded footwear system may be only a footwear sole such as a footwear insole. For example, the footwear may be a shoe having a shoe sole (footwear sole) and a shoe body (footwear body). In another example, the footwear may be a footwear sole such as a shoe insole, which is a separate layer that can be placed in any shoes.

By using the disclosed compass-sensor embedded footwear system, foot directional information and foot gesture information of human foot/feet, wearing the footwear, may be obtained.

According to the present disclosure, in one embodiment, foot and/or user directional information and a range of foot gesture information from a user's feet may be effectively provided to a device/devices such as smart phones, tablets, game consoles, computers, to achieve natural hand-free user experiences for navigation in simulated virtual world, for example, in gaming applications and other types of applications. In one embodiment, products based on the present disclosure may be a new type of foot-wearing input device for computers, smart phones, tablet, game console, etc.

As used herein, the term "foot directional information" refers to direction(s) that foot/feet in operation point at. The term "foot directional information" and "foot pointing information" may be interchangeably used in the present disclosure.

As used herein, the term "foot gestures" may include simple gestures, such as taps by foot/feet, and complex gesture behaviors, such as walking, jumping, running, etc.

FIG. 1 illustrates components of an exemplary compass-sensor embedded footwear system in accordance with various embodiments of the present disclosure. The compass-sensor embedded footwear system illustrated in FIG. 1 may include a left footwear and/or a right footwear, which may include a shoe including a shoe body and a shoe sole. Although not shown in FIG. 1, all components in this exemplary system may be configured in a shoe insole.

In various embodiments, two pressure sensors 102 and 107 may be embedded in the left footwear sole 106 at locations corresponding to a bottom of a human left foot. For example, pressure sensor 107 may be positioned at a location corresponding to a center of a fore-foot (or a center of ball of foot) of a human left foot sole denoted as sole area A, pressure sensor 102 may be positioned at a location corresponding to a center of a back-foot (or a center of heel) of a human left foot sole denoted as sole area B.

In various embodiments, two pressure sensors 202 and 207 may be embedded in the right footwear sole 206 at locations corresponding to a bottom of a human right foot. For example, pressure sensor 207 may be positioned at a location corresponding to a center of a fore-foot (or a center of ball of foot) of a human right foot sole denoted as sole area C, pressure sensor 202 may be positioned at a location corresponding to a center of a back-foot (or a center of heel) of a human right foot sole denoted as sole area D.

In various embodiments, a compass sensor 105/205 maybe embedded in the left/right footwear sole 106/206 or installed on the outer surface of the left/right footwear, at a fixed location and with a fixed orientation with respect to the left/right footwear sole 106/206. The compass sensor 105/205 is placed such that when the left/right footwear sole 106/206 is substantially leveled in a horizontal position, the compass sensor 105/205 is in normal operation.

In various embodiments, a control-communication unit 103/203 and a battery module 104/204 may be placed inside or on the outer surface of the left/right footwear 106/206 to support operation of the left/right footwear and its communication with e.g., external devices, such as smart phones, computers, game consoles, etc.

The control-communication unit 103/203, battery module 104/204, compass sensor 105/205 and pressure sensors 102,107/202,207 are connected with wires inside the left/right footwear for power, control and communication.

Figure 2:
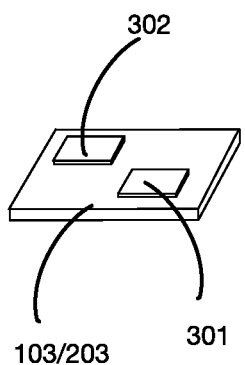
FIG. 2 illustrates an exemplary control-communication unit used in the compass-sensor embedded footwear system in FIG. 1 according to various embodiments of the present disclosure.

FIG. 2 further illustrates components of a control-communication unit 103/203, which has a processor module 301 and a wireless communication module 302, e.g., a blue tooth communication module.

For the compass-sensor embedded footwear system, various different configurations, placements, and/or arrangements of the battery module 104/204, control-communication unit 103/203, and compass sensor 105/205 may be included. This may in turn provide different tradeoffs among system performance, footwear appearance, and wearing comfort level.

In a first exemplary type of component arrangement configuration, or exemplary component arrangement configuration 1, the battery module 104/204, control-communication unit 103/203, and compass sensor 105/205, are all embedded in the footwear, for example in the footwear sole 106/206. In this configuration, a charging inlet 101/201 is also provided on each footwear, either on a footwear sole or a footwear body.

The exemplary component arrangement configuration 1 in FIG. 1 has a minimum impact on appearance of the footwear. However, hiding all components inside the footwear bodies may negatively affect system performance in terms of operation hours per charge, and footwear wearing comfort level.

The exemplary component arrangement configuration 1 may allow the footwear to be in forms of shoes as shown in FIG. 1, although, not shown in FIG. 1, this exemplary component arrangement configuration 1 can be adapted into shoe insoles.

Figure 3:
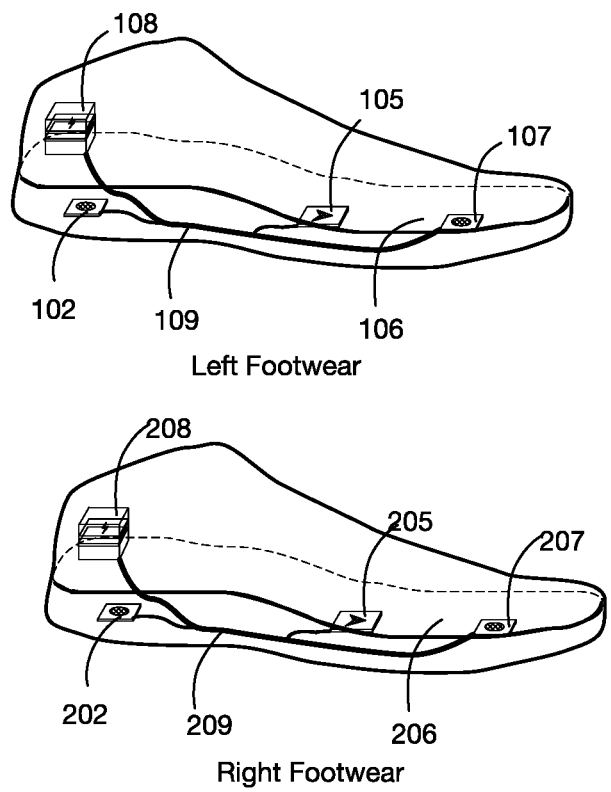
FIG. 3 illustrates another exemplary compass-sensor embedded footwear system according to various embodiments of the present disclosure.

The second exemplary type of component arrangement configuration, or an exemplary component arrangement configuration 2, is illustrated in FIG. 3. In this configuration, the battery module and the control-communication unit are placed on the outer surface of the footwear, for example, attached to an outer surface of the footwear body and/or footwear sole of the footwear.

Figure 4:
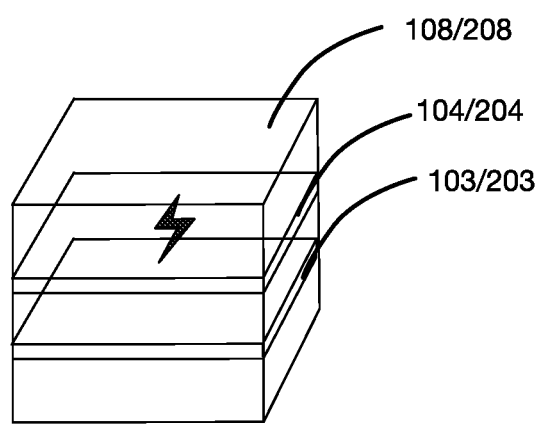
FIG. 4 illustrates an exemplary power-control-communication unit used in the compass-sensor embedded footwear system in FIG. 3 according to various embodiments of the present disclosure.

In various embodiments with component arrangement configuration 2, battery module 104/204 and the control-communication unit 103/203 may be combined as a single power-control-communication unit 108/208 as illustrated in FIG. 4. The single power-control-communication unit 108/208 may be installed on the outer surface of the footwear. The power-control-communication unit 108/208 is connected to sensors in the left/right footwear by cables 109/209 that run inside the left/right footwear for power supply, control and communication.

In various embodiments with component arrangement configuration 2, the power-control-communication unit 108/208 may be detachable and re-attachable to the footwear using a proper connector or clip.

Component arrangement configuration 2 may allow the separation of the left/right footwear into two parts. One part is a separate insole layer, containing the pressure sensors and the compass sensor. The other part is the shoe part (e.g., including a shoe body and a shoe sole) on which the battery-control-communication unit may be installed. The two parts of the footwear may be connected by a proper connector and wires for power, control and communication.

Component arrangement configuration 2 may have certain impact on the footwear's appearance. However, installing components for power, communication and control on the outer surface of the footwear may improve system performance, e.g., operation hours per charge, as well as footwear wearing comfort level. The optional detachable feature of the power-control-communication unit allowed by this component arrangement configuration may also make the charging, communication pairing and maintenance processes easier to improve user experiences, and support the use of the same left/right power-control-communication unit with different left/right footwear.

Figure 5:
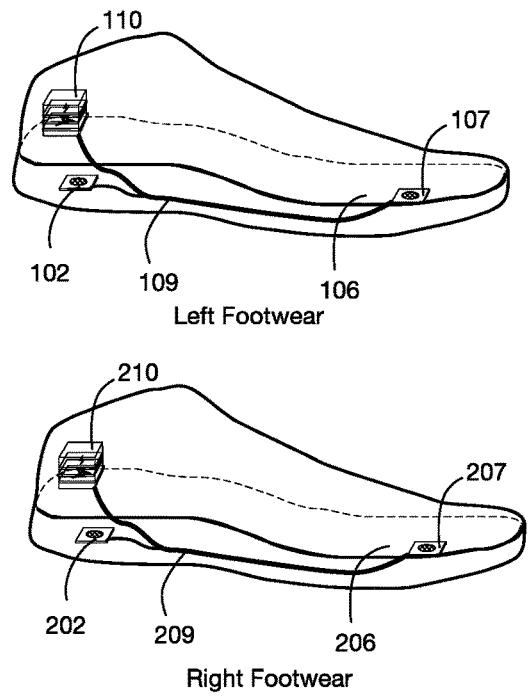
FIG. 5 illustrates another exemplary compass-sensor embedded footwear system according to various embodiments of the present disclosure.

The third exemplary type of component arrangement configuration, or an exemplary component arrangement configuration 3, is illustrated in FIG. 5. In this configuration, the battery module, the control-communication unit and the compass sensor are placed on the outer surface of the footwear.

Figure 6:
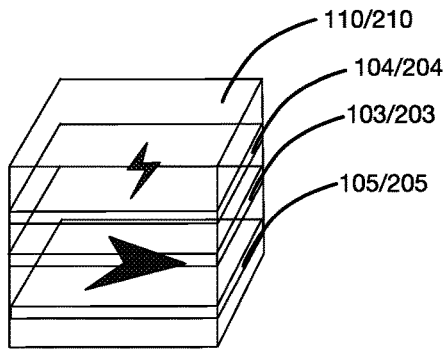
FIG. 6 illustrates an exemplary power-control-communication-compass unit used in the compass-sensor embedded footwear system in FIG. 5 according to various embodiments of the present disclosure.

In various embodiments with component arrangement configuration 3, the battery module 104/204, control-communication unit 103/203, and the compass sensor 105/205 are combined into a single power-control-communication-compass unit 110/210. The power-control-communication-compass unit 110/210 illustrated in FIG. 6 may be installed on the outer surface of the footwear. The power-control-communication-compass unit 110/210 is connected to pressure sensors in the left/right footwear by cables 109/209 that run inside the left/right footwear for power supply, control and communication.

In various embodiments with component placement configuration 3, the power-control-communication-compass unit 110/210 may be detachable and re-attachable to the left/right footwear using a proper connector or clip. A detachable power-control-communication-compass unit 110/210 may also be used with different left/right footwear.

Component arrangement configuration 3 may allow the separation of the footwear into two parts. One part is a separate insole layer, containing only the pressure sensors. The other part is a shoe part (e.g., including a shoe body and a shoe sole) on which the battery-control-communication-compass unit is installed. The two parts of the footwear may be connected by a proper connector and wires for power, control and operation.

Compared to component arrangement configuration 2, component arrangement configuration 3 may further improve wearing comfort level of the compass-sensor embedded footwear system by leaving only the two pressure sensors inside the footwear sole. The footwear sole may be a separate insole layer or may be a shoe sole of the shoe footwear. However, it requires the power-control-communication-compass unit 110/210 to be placed such that it has a fixed orientation with respect to the footwear sole 106/206, and the integrated compass sensor 105/205 is in normal operation when the corresponding footwear sole 106/206 is substantially leveled in a horizontal position.

The disclosed system features a novel combined use of information from the left and right footwear. With the compass sensors, user's foot pointing directions, alternatively referred to as foot directional information, may be obtained in the user's local North-East coordinate system. The pressure sensors are able to provide pressure measurements at designed user sole areas. The foot directional information, used in conjunction with pressure measurements, may provide (user) directional information on a user's intended movements, and support complex foot gesture detections. The foot and/or user directional information and foot gesture detection results from the compass-sensor embedded footwear system may support various gaming applications and other types of applications for controls and, especially, hand-free navigation in simulated virtual world, to provide unique and improved user experiences.

Figure 7:
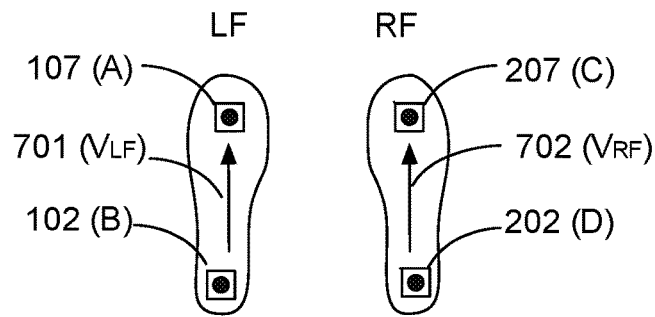
FIG. 7 illustrates an exemplary arrangement of pressure sensors at designed sole areas according to various embodiments of the present disclosure.

For example, FIG. 7 illustrates arrangement of pressure sensors at four designed sole areas with respect to the contours of both human feet, and the corresponding left foot direction vector and right foot direction vector.

As shown in FIG. 7, the locations of the pressure sensors, e.g., on the designed sole areas A, B, C and D, may be with respect to contours of left and right soles. Sole area A corresponds to a center of a fore-foot (or a center of ball of foot) of a human left foot. Sole area B corresponds to a center of a back-foot (or a center of heel) of a human left foot. Sole area C corresponds to a center of a fore-foot (or a center of ball of foot) of a human right foot. Sole area D corresponds to a center of a back-foot (or a center of heel) of a human right foot. At a certain data sampling time pressure level measurements from pressure sensors 102, 107, 202 and 207 may be denoted as $P_A$, $P_B$, $P_C$ and $P_C$, respectively.

FIG. 7 also illustrates foot direction vectors $V_{LF}$ (701) for a human left foot and $V_{RF}$ (702) for a human right foot, which are aligned with the directions to which the corresponding foot is pointing at when a user is wearing the footwear.

Figure 8:
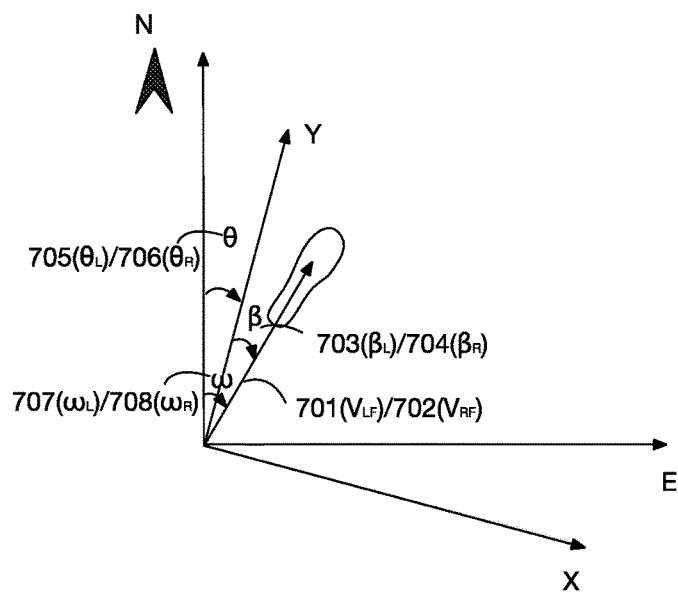
FIG. 8 illustrates an exemplary relationship between a user's local North-East (N-E) coordinate system, a compass sensor's own reference X-Y 2 dimensional (2D) coordinate system, and a foot direction vector according to various embodiments of the present disclosure.

FIG. 8 illustrates an exemplary relationship between the user's local North-East (N-E) coordinate system, a compass sensor's own reference X-Y 2D coordinate system, and a foot direction vector. In FIG. 8 the N axis corresponds to the user's local North direction, and the E axis corresponds to the user's local East direction. The Y axis corresponds to a compass sensor's reference 2D coordinate Y. The X axis corresponds to a compass sensor's reference 2D coordinate X. Angle θ (705/706) is the angle from the North N axis to the Y axis, which can be obtained from compass sensor measurements.

Vector $V_{LF}$ or $V_{RF}$ corresponds to the foot direction vector 701/702 for left/right foot. Angle β (703/704) is the angle from the Y axis of a compass's reference coordinate system to a left/right foot direction vector 701/702. Once a compass sensor 105/205 is installed to the left/right footwear with a fixed orientation with respect to the left/right footwear sole 106/206, β (703/704) is fixed and can be easily measured/obtained. Angle ω is the sum of θ and β, which is a foot (footwear) pointing direction angle in the user's local North-East (N-E) coordinate system, i.e., the angle from the local North (N) axis to the foot direction vector. For left foot, the foot pointing direction angle ω is denoted as $\omega_L$ (707), and for right foot, the foot pointing direction angle ω is denoted as $\omega_R$ (708). For each foot, the local processor 301 is able to obtain θ (705/706) from the compass sensor and then evaluate the foot pointing direction angle ω (707/708) in the local North-East 2D coordinate system with the pre-obtained (703/704) of the corresponding left/right footwear.

Figure 9:
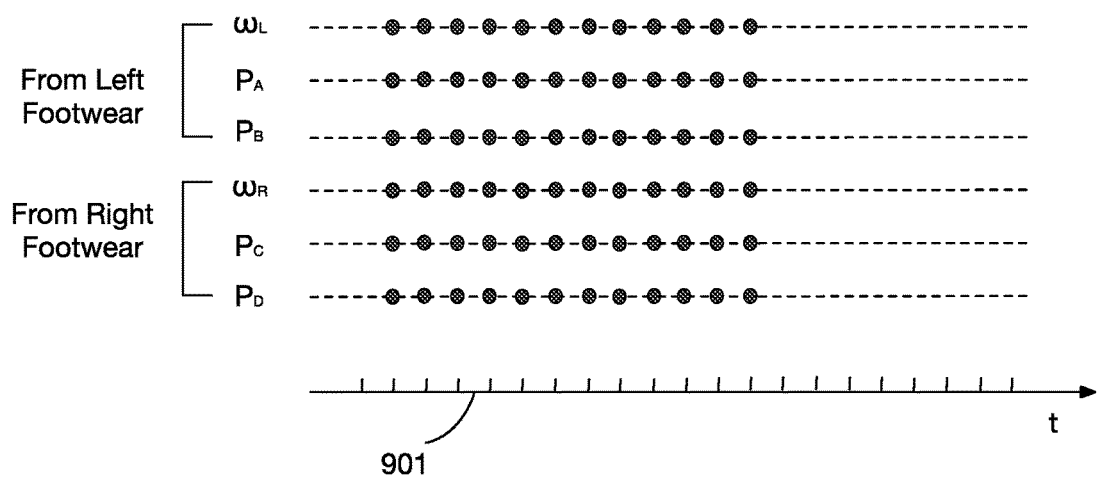
FIG. 9 illustrates exemplary left and right footwear measurement-information sets in a compass-sensor embedded footwear system at data sampling times according to various embodiments of the present disclosure.

FIG. 9 summarizes the flows of measurements/derived measurements in the compass-sensor embedded footwear system over time. The sampling time interval is denoted as 901. The uniform sampling time interval illustrated in FIG. 9 is only for illustration purpose. At each data sampling time, the compass sensor (105/205) of the left/right footwear provides a $\theta_L/\theta_R$ measurement (705/706), which is used to obtain $\omega_L/\omega_R$ (707/708) in the local N-E coordinate system with the pre-obtained $\beta_L/\beta_R$ (703/704). The pressure sensors (107 and 102) of the left footwear provide pressure measurements $P_A$ and $P_B$ at the corresponding sole areas. The pressure sensors (207 and 202) of the right footwear provide pressure measurements $P_C$ and $P_D$ at the corresponding sole areas. At each sampling time, the obtained $\omega_L$ 707/$\omega_R$ 708, and pressure measurements $(P_A, P_B)/(P_C, P_D)$ form a left/right footwear measurement-information set.

Figure 10:
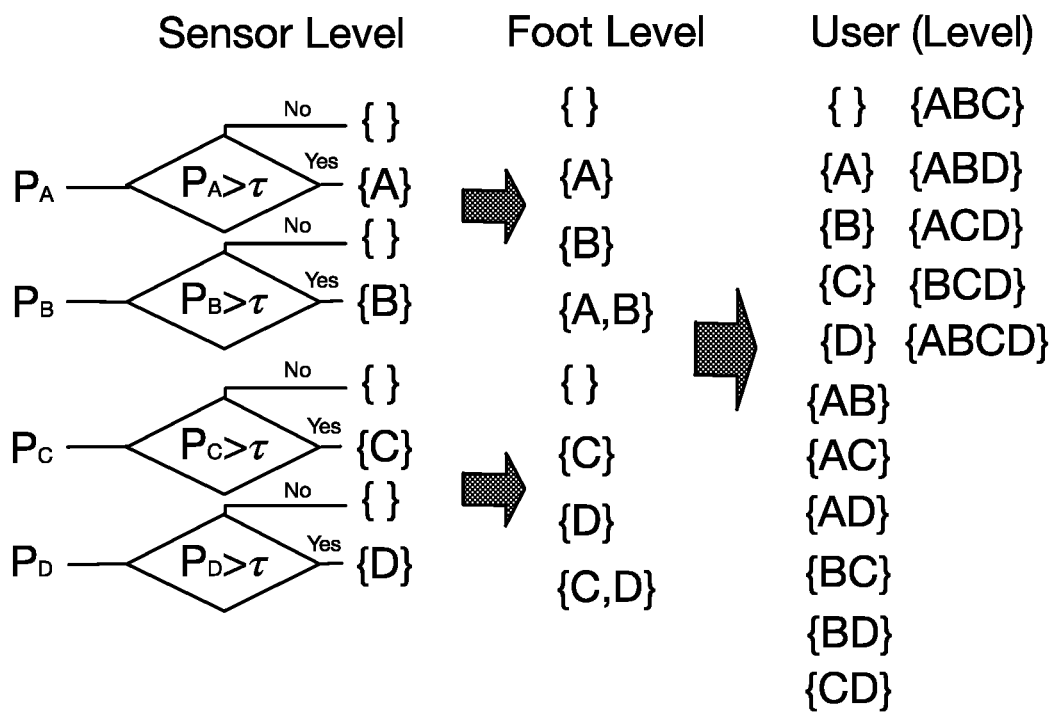
FIG. 10 illustrates processing of pressure sensor measurements to obtain sole area touch detection results, foot-level touch detection results, and a user touch detection outcome at a data sampling time according to various embodiments of the present disclosure.
Figure 11:
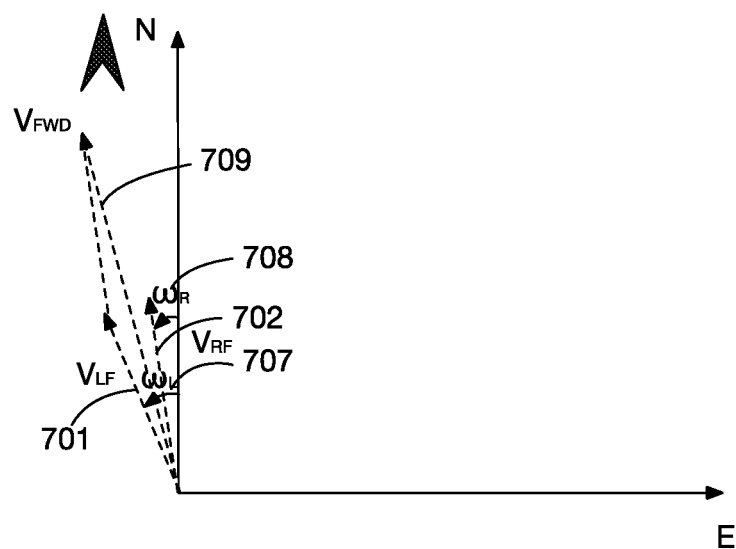
FIG. 11 illustrates a user forward direction vector $V_{FWD}$ obtained by fusing foot direction vectors from both feet according to various embodiments of the present disclosure.

At a data sampling time, pressure measurements $P_A$, $P_B$, $P_C$ and $P_D$ may be used together to obtain a user (foot) touch detection outcome. As illustrated in FIG. 10, the pressure measurement from each sensor is first compared to a pre-set threshold level τ, above which a touch of the corresponding sole area touch is detected. The sensor-level sole area touch detection results that correspond to the left or right foot may be combined to produce foot-level touch detection results. As illustrated in FIG. 10, for each foot, a foot-level touch detection result may fall in a set of four possible outcomes, denoted as { }, {A}, {B} and {A B} for left foot, and { }, {C}, {D}, {C D} for right foot. Combining the foot-level touch detection results for both feet, a user (level) touch detection outcome at a data sampling time may be obtained, which has 16 possible outcomes as an example listed in FIG. 10 ranging from { } (no-touch) to {A B C D} (full-touch). User touch detection outcomes at current and previous sampling times may be used for simple and complex gesture detections.

The foot pointing direction angles $\omega_L$ (707) and $\omega_R$ (708) provide foot directional information in a common local N-E coordinate system, which may be further fused to obtain user directional information. FIG. 10 illustrates fusion of $\omega_L$ (707) and $\omega_R$ to obtain a fused user (forward) directional vector $V_{FWD}$ 709 that reveals the information on the wearer's (user's) intended movement direction. The fused user directional information can be provided as valuable user information/controls to other applications that run on external devices, e.g., a computer, a game console, and/or a smart phone, connected to the disclosed system through wireless communication links.

As shown in FIG. 10, foot pointing direction angles $\omega_L$ (707) and $\omega_R$ (708) may be converted to foot direction vectors $V_{LF}$ (701) and $V_{RF}$ (702) in the local N-E coordinate system. FIG. 10 illustrates an exemplary simple way that may be used to obtain $V_{FWD}$ (709) as the vector sum of $V_{LF}$ (701) and $V_{RF}$ (702). Other method for deriving $V_{FWD}$ (709) may use the pressure measurements $P_A$, $P_B$, $P_C$, and $P_D$, since, when a user applies different pressure to each foot, the pointing direction of the foot that has more pressure bears more information on $V_{FWD}$. For example, when a person stands on one foot, his or her natural movement direction is mostly determined by the pointing direction of the standing foot.

Figure 12:
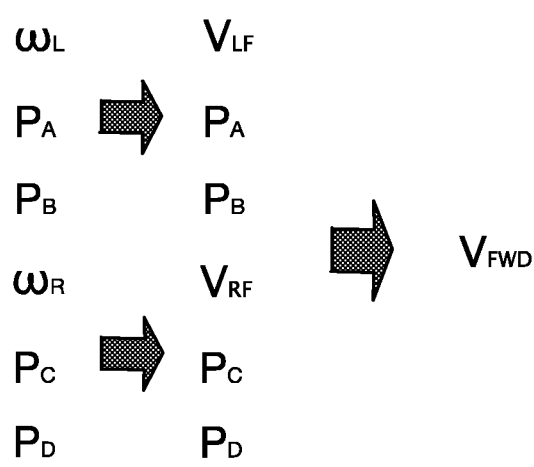
FIG. 12 illustrates joint processing and fusion of left and right foot direction vectors as well as the pressure sensor measurements to derive a user forward direction vector $V_{FWD}$ according to various embodiments of the present disclosure.

FIG. 12 illustrates an information processing flow to obtain $V_{FWD}$ (709). First from the left and right footwear measurement-information sets, the foot pointing direction angles $\omega_L$ (707) and $\omega_R$ (708) are converted to foot direction vectors $V_{LF}$ (701) and $V_{RF}$ (702) in the local N-E coordinate system. Then the converted $V_{LF}$ (701) and $V_{RF}$ (702), along with pressure measurements $P_A$, $P_B$, $P_C$, and $P_D$ may be processed jointly to produce the user (forward) directional vector $V_{FWD}$. For example, one processing method may be:

$$V_{FWD} = \frac{P_A + P_B}{P_A + P_B + P_C + P_D} V_{LF} + \frac{P_C + P_D}{P_A + P_B + P_C + P_D} V_{RF}$$

which uses a weighted combination of $V_{LF}$ and $V_{RF}$ according to the pressure measurements. Another processing method to obtain $V_{FWD}$ may be:

$$V_{FWD} = \begin{cases} V_{LF}, & \text{if } \tau_1 < P_A + P_B \text{ and } P_C + P_D \leq \tau_1 \\ \frac{P_A + P_B}{P_A + P_B + P_C + P_D} V_{LF} + \\ \frac{P_C + P_D}{P_A + P_B + P_C + P_D} V_{RF}, & \text{if } \tau_1 < P_A + P_B \text{ and } \tau_1 < P_C + P_D \\ V_{RF}, & \text{if } \tau_1 < P_C + P_D \text{ and } P_A + P_B \leq \tau_1 \end{cases}$$

where $\tau_1$ is a pressure level threshold. If the total pressure level on a foot is below the corresponding foot direction vector should not be used for the evaluation of $V_{FWD}$. Other method for the evaluation of user directional information can be devised to best suit certain applications. In the present disclosure, the joint use of measurements from the pressure sensors at the designed sole areas, and the foot pointing directional information from the compass sensor is able to provide valuable user (movement) directional information.

In addition to providing foot directional and user directional information, the combined use of the foot directional information, the user touch detection outcomes and the pressure sensor measurements can be used for basic and complex foot gesture detections.

Referring back to FIG. 10, at each sampling time, a user touch detection outcome, such as {A}, {A B}, {A B C D}, {C}, { }, etc., corresponds to a set of detected (ground) touches by different sole areas. For example, the empty set { } that corresponds to no (ground) touch detection is made by any sole area at the data sampling time.

To define foot gestures, a touch detection state is defined as a combined set of one or multiple possible user touch detection outcomes. For example, touch detection state {A&B&C} (where "&" is the "and" operator) means the touch detection state requires the detection of touches from sole areas A, B and C. As a result, only user touch detection outcome {A B C} belongs to the touch detection state.

As another example, touch detection state {A} {B} (where "|" is the "or" operator) means the touch detection state requires a touch detection in sole area A or B. As a result, user touch detection outcomes {A} {B} and {A B} satisfy the touch detection state requirement, and would belong to touch detection state {A|B}.

When there is only one or none sole area touch detected, e.g., user touch detection outcome {A}, and { }, the user touch detection outcome has the same notation as the detection state that containing only the detection outcome.

Further, a touch detection state transition is defined as when the user touch detection outcome moves from one touch detection state to a different touch detection state. When a user touch detection outcome at a sampling time belongs to the same touch detection state as the previous user touch detection outcome, there is no touch detection state transition.

In the present disclosure, foot gestures are defined and determined based on transitions between touch detection states in conjunction with foot directional information from foot direction vectors. Exemplary foot gestures are defined as follows.

Left foot tap type 1: tap with the front part of left foot. The touch detection states follow transition sequence {A&B&C&D}→{B&C&D}→{A&B&C&D}→ {B&C&D}→{A&B&C&D}.

Both the calculated left foot direction vector $V_{LF}$ 701 (or equivalently the left foot pointing direction angle $\omega_L$ 707) and the calculated right foot direction vector $V_{RF}$ 702 (or equivalently the right foot pointing direction angle $\omega_R$ 708) in the N-E coordinate system remain roughly the same.

Note that the touch detection state transition sequence may repeat itself for multiple times.

Left Foot Tap Type 2: Tap with the Heel Part of Left Foot.

The touch detection states follow transition sequence {A&B&C&D}→{A&C&D}→{A&B&C&D}→{A&C&D}→{A&B&C&D}.

Both the calculated left foot direction vector $V_{LF}$ 701 (or equivalently the left foot pointing direction angle $\omega_L$ 707) and the calculated right foot direction vector $V_{RF}$ 702 (or equivalently the right foot pointing direction angle $\omega_R$ 708) in the N-E coordinate system remain roughly the same.

Right Foot Tap Type 1: Tap with the Front Part of Right Foot.

The touch detection states follow transition sequence {A&B&C&D}→{A&B&D}→{A&B&C&D}→{A&B&D}→{A&B&C&D}.

Both the calculated left foot direction vector $V_{LF}$ 701 (or equivalently the left foot pointing direction angle $\omega_L$ 707) and the calculated right foot direction vector $V_{RF}$ 702 (or equivalently the right foot pointing direction angle $\omega_R$ 708) in the N-E coordinate system remain roughly the same.

Right Foot Tap Type 2: Tap with the Heel Part of Right Foot.

The touch detection states follow transition sequence {A&B&C&D}→{A&B&C}→{A&B&C&D}→{A&B&C}→{A&B&C&D}.

Both the calculated left foot direction vector $V_{LF}$ 701 (or equivalently the left foot pointing direction angle $\omega_L$ 707) and the calculated right foot direction vector $V_{RF}$ 702 (or equivalently the right foot pointing direction angle $\omega_R$ 708) in the N-E coordinate system remain roughly the same.

One-Foot Hop Type 1: Left Foot Hop.

The touch detection states follow transition sequence {A|B}→{ }→{A|B}→{ }→{A|B}→{ }.

Note that touch detection state {A|B} consists of three possible user touch detection outcomes {A}, {B} and {A B}. In this case, even when the user touch detection outcome changes from {A} to {A B}, there is no touch detection state transition.

One-Foot Hop Type 2: Right Foot Hop.

The touch detection states follow transition sequence {C|D}→{ }→{C|D}→{ }→{C|D}→{ }.

Jump Using Both Feet.

The touch detection states follow transition sequence {A|B|C|D}→{ }→{A|B|C|D}→{ }→{A|B|C|D}.

Left Foot Wiggle Type 1: Left Foot Wiggle with the Front of the Left Foot as the Pivot.

The touch detection state stays at {(A&C&D)|(A&B&C&D)} which covers two possible user touch detection outcomes {A C D} and {A B C D}.

The calculated left foot direction vector, $V_{LF}$ 701 in the N-E coordinate system wiggles from side to side.

The calculated right foot direction vector, $V_{RF}$ 702 in the N-E coordinate system stays roughly the same.

Left Foot Wiggle Type 2: Left Foot Wiggle with the Heel of the Left Foot as the Pivot.

The touch detection state stays at {(B&C&D)|(A&B&C&D)} which covers two possible detection sets {B C D} and {A B C D}.

The estimated left foot direction vector, $V_{LF}$ 701 in the N-E coordinate system wiggles from side to side.

The calculated right foot direction vector, $V_{RF}$ 702 in the N-E coordinate system stays roughly the same.

Right Foot Wiggle Type 1: Right Foot Wiggle with the Front of the Right Foot as the Pivot.

The touch detection state stays at {(A&B&C)|(A&B&C&D)}.

The estimated right foot direction vector, $V_{RF}$ 702 in the N-E coordinate system wiggles from side to side.

The calculated left foot direction vector, $V_{LF}$ 701 in the N-E coordinate system stays roughly the same.

Right Foot Wiggle Type 2: Right Foot Wiggle with the Heel of the Right Foot as the Pivot.

The touch detection state stays at {(A&B&D)|(A&B&C&D)}.

The estimated right foot direction vector, $V_{RF}$ 702 in the N-E coordinate system wiggles from side to side.

The calculated left foot direction vector, $V_{LF}$ 701 in the N-E coordinate system stays roughly the same.

For gesture detections, pressure measurements $P_A$, $P_B$, $P_C$ and $P_D$ may provide additional feature information for detected gestures, which allows, the further differentiation of gestures of the same type, e.g., the differentiation between small jumps and big jumps.

Figure 13:
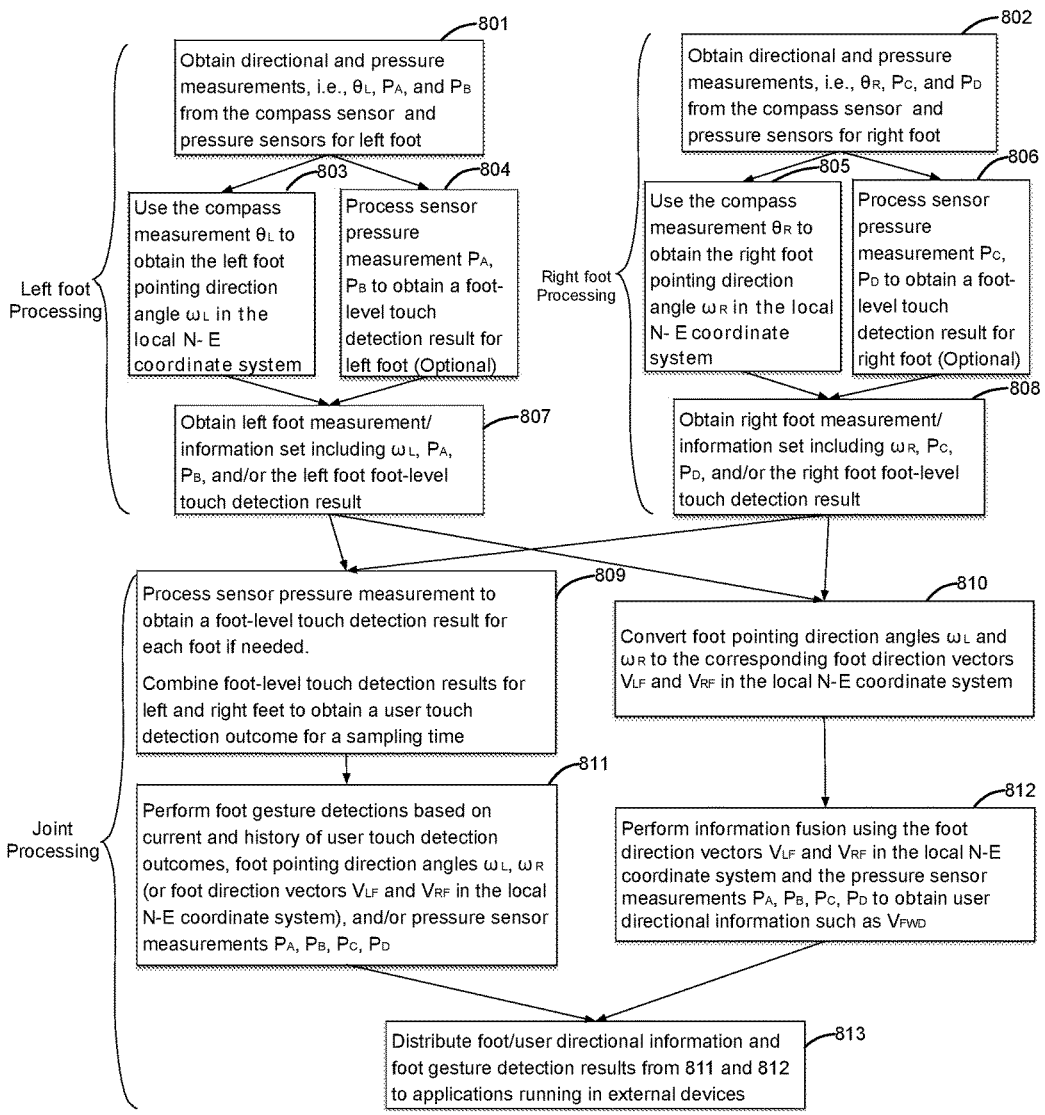
FIG. 13 illustrates an information processing flow at a data sampling time in a compass-sensor embedded footwear system according to various embodiments of the present disclosure.

FIG. 13 summarizes the information processing flow at a data sampling time in the compass-sensor embedded footwear system. The processing flow starts from measurement collection at the left and the right footwear, as shown in Step 801 and Step 802, where compass measurement $\theta_L$ 705/$\theta_R$ 706 is read from the compass sensor 105/205 of the left/right footwear. In step 801/802, pressure measurements ($P_A$, $P_B$)/($P_C$, $P_D$) are read from the left/right footwear pressure sensors (102,107)/(202,207).

In Step 803/805, the compass measurements $\theta_L$/$\theta_R$ (705/706) from Step 801/802 are processed with the pre-obtained $\beta L$/$\beta R$ (703/704) to obtain $\omega_L$/$\omega_R$ (707/708), which is the left/right foot pointing direction angle in the local North-East 2D coordinate system.

In Step 804/806, pressure measurements ($P_A$, $P_B$)/($P_C$, $P_D$) from Step 801/802 are processed according to FIG. 10 to obtain a foot-level touch detection result for the left/right foot. Note that this Step 804/806 is optional, since the same process can also be performed later in Step 809 as shown in FIG. 13.

In Step 807/808, results from Step 803/805 and 804/806 are combined to obtain a left/right footwear measurement-information set from the left/right footwear at each sampling time, including $\omega_L$/$\omega_R$ (707/708) from step 803/805, ($P_A$, $P_B$)/($P_C$, $P_D$) and/or a left/right foot-level touch detection result from step 804/806.

By performing Steps 809 and 811, the measurement-information set from Step 807 for the left footwear and the measurement-information set from Step 808 for the right footwear are gathered together and jointly processed for foot gesture detections.

In Step 809, pressure measurements ($P_A$, $P_B$) from Step 807 for the left footwear and ($P_C$, $P_C$) from Step 808 for the right footwear are jointly processed to obtain the user touch detection outcome of the data sampling time, in the case that results from Step 807 and/or 808 do not have foot-level touch detection results. In the case that the left and right foot-level touch detection results are available from Steps 807 and 808, they can be directly combined in Step 809 to obtain the user touch detection outcome.

In Step 811, gesture detections are performed based on current and history of user touch detection outcomes from Step 809, foot pointing direction angles $\omega_L$ (707), $\omega_R$ (708) from Steps 807 and 808 (which may be converted to foot direction vectors $V_{LF}$ (701) and $V_{RF}$ (702) in the local N-E coordinate system), and/or pressure sensor measurements $P_A$, $P_B$, $P_C$, and $P_D$ from Steps 807 and 808.

By preforming Steps 810 and 812, the measurement-information set from Step 807 for the left footwear and the measurement-information set from Step 808 for the right footwear are gathered together and jointly processed to obtain fused user directional information, such as $V_{FWD}$ (709).

In Step 810, the foot pointing direction angles $\omega_L$ (707) and $\omega_R$ (708) from Steps 807 and 808 may be converted to the corresponding foot direction vectors $V_{LF}$ (701) and $V_{RF}$ (702) in the local N-E coordinate system.

In Step 812, the foot direction vectors $V_{LF}$ (701) and $V_{RF}$ (702) in the local N-E coordinate system from Steps 810 and the pressure sensor measurements $P_A$, $P_B$, $P_C$, and $P_D$ from Steps 807 and 808 are further fused to obtain user directional information, such as $V_{FWD}$, according to various fusion methods devised for different types of applications.

In Step 813, foot gesture detection results from Step 811 and foot/user directional information from Step 812 are sent/dispatched to targeting applications of the compass-sensor embedded footwear system that may run in external device(s).

As such, by performing Steps 809, 810, 811 and 812, the information processing processes for foot gesture detections and user directional information extractions require the joint process of data and information from both feet. As a result, data and information originated from the left footwear and the right footwear need to be gathered together and processed at one place. Two types of system operation configurations may be used to address the problem, for example, as shown in FIGS. 14-15.

Figure 14:
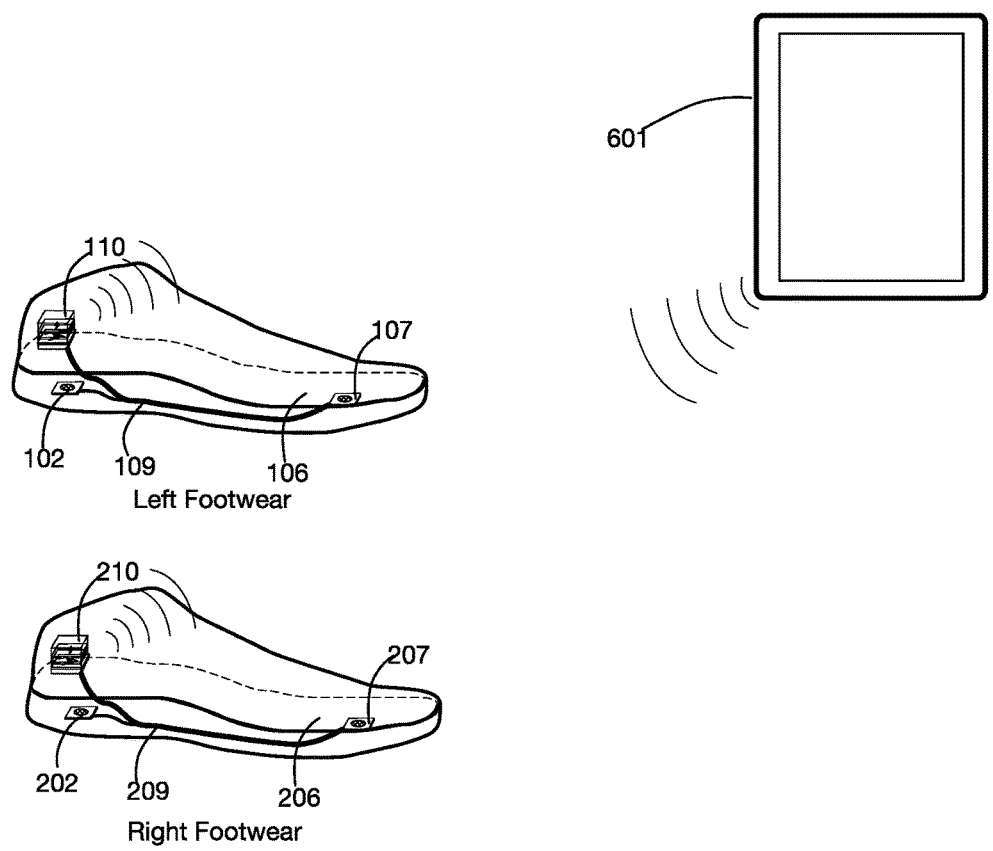
FIG. 14 illustrates an exemplary system operation configuration including a compass-sensor embedded footwear system and an external device according to various embodiments of the present disclosure.

FIG. 14 illustrates an exemplary system operation configuration including a compass-sensor embedded footwear system and an external device, where both the left footwear and right footwear communicate simultaneously with the external device In the exemplary system operation configuration shown in FIG. 14, the joint processing of left and right foot information, e.g., Steps 809-812 in FIG. 13, is done at an external device to which both the left footwear and the right footwear are connected. In this configuration, footwear measurement-information sets as shown in FIG. 9 and/or the foot-level touch detection results in FIG. 10 from both the left and the right footwear are sent through wireless links to the external device. The remaining processing for further fusion of the information and gesture detections are done at the external device by a software driver.

Figure 15:
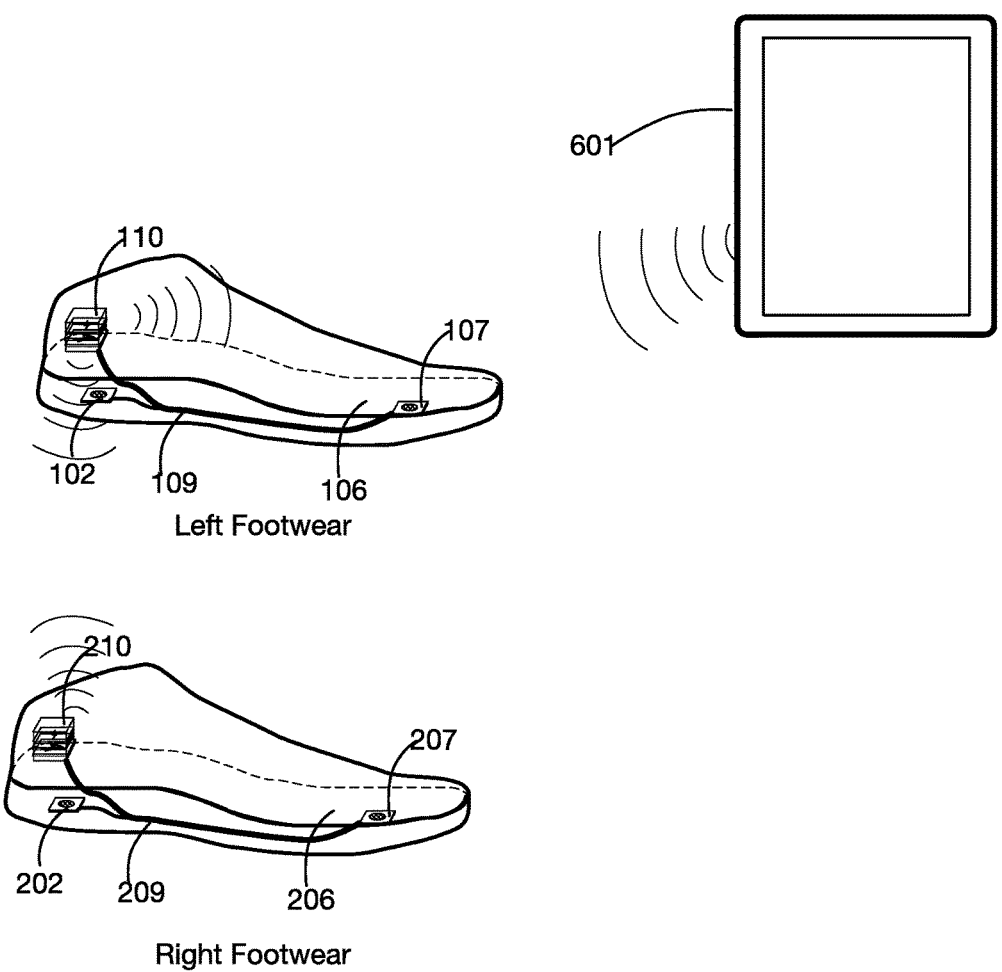
FIG. 15 illustrates another exemplary system operation configuration including a compass-sensor embedded footwear system and an external device according to various embodiments of the present disclosure.

FIG. 15 illustrates another exemplary system operation configuration when the compass-sensor embedded footwear system works with an external device, where the footwear for one foot (e.g., left foot) is configured as master, and the footwear for the other foot (e.g., right foot) is configured as slave.

In the exemplary system operation configuration shown in FIG. 15, the joint processing of left and right foot information, e.g., Steps 809-812 in FIG. 13, is done at the left (or right) footwear that acts as a system master. The other footwear acts as a slave device. A wireless communication link, e.g., a blue tooth link, is established between the master and the slave. At the sampling times, the salve send its local measurement-information set, e.g., as illustrated in FIG. 9, and/or foot-level touch detection result, as illustrated in FIG. 10, to the master where the joint processing of left and right foot information may be performed. The master has another wireless communication connection with the remote device, through which controls/information requests for the sensor-embedded footwear system from the external device can be received, and foot directional information, user directional information and/or foot gesture detection results may be sent to the external device.

The present disclosure is able to obtain rich action and gesture information from human feet that are not available from existing hand operation based systems. Outputs from the present disclosure can be used for device control, video game applications, interactive 3D programs and virtual reality applications to support hand-free navigation in simulated virtual worlds.

The above detailed descriptions only illustrate certain exemplary embodiments of the present invention, and are not intended to limit the scope of the present invention. Those skilled in the art can understand the specification as whole and technical features in the various embodiments can be combined into other embodiments understandable to those persons of ordinary skill in the art. Any equivalent or modification thereof, without departing from the spirit and principle of the present invention, falls within the true scope of the present invention.

What is claimed is:

1. A method for using an improved compass-sensor embedded footwear system comprising:
    at a data sampling time, obtaining pressure measurements from pressure sensors embedded in a left footwear and/or a right footwear;
    based on the pressure measurements, determining sole area touch detection results corresponding to ground touches made by areas on each footwear sole of the left footwear and/or the right footwear;
    obtaining compass measurements from a compass sensor in each of the left and/or right footwears to provide an angle from a North direction of a local North-East coordinate system to an axis of the compass sensor's reference coordinate system;
    obtaining a relationship between the compass sensor's reference coordinate system and a corresponding foot pointing direction based on the compass-sensor embedded footwear system; and
    based on the obtained relationship and the angle from the compass measurements, evaluating the left and/or right foot pointing direction angles in the local North-East coordinate system.

2. The method according to claim 1, further including:
    processing the information, including:
    combining the sole area touch detection results from the left footwear and/or the right footwear to obtain a user touch detection outcome at each data sampling time; and
    determining foot gestures based on current and history information of: the user touch detection outcomes, the left and/or right foot pointing direction angles, and/or pressure measurements from the pressure sensors.

3. The method according to claim 1, wherein:
    a pressure measurement from each pressure sensor is compared to a threshold level to determine if the corresponding sole area is in touch with the ground to provide a sole area touch detection result.

4. The method according to claim 1, further including:
    transmitting the information including the sole area touch detection results, the foot pointing direction angles for the left footwear and/or the right footwear to an external device for further processing and control purposes.

5. The method according to claim 2, wherein:
    processing the information from the left and/or right footwears is conducted by one of the left or right footwear as a master footwear; and
    the master footwear sends the foot directional information and foot gesture detection results to an external device through another a wireless communication link.

6. The method according to claim 1, further comprising:
repeating each step at every sampling time performed by the compass-sensor embedded footwear system.

7. An improved method for detecting user foot gestures, comprising:
defining a user foot gesture as a transition sequence of touch detection states in conjunction with foot pointing directions of a user's left foot and/or right foot, wherein:
a touch detection state is a set of one or multiple possible user touch detection outcomes, and
a user touch detection outcome corresponds to a detection of none, one, or multiple of two or four designed sole areas, at a fore part and a heel part of the user's left foot and/or the user's right foot, touching to the ground;
at each sampling time, obtaining a user touch detection outcome corresponding to the designed sole areas at the user's left foot and/or the user's right foot;
at each sampling time, obtaining a user foot pointing direction in a reference coordinate system; and
at each sampling time, checking if the defined user foot gesture is matched by the current and history user touch detection outcomes and/or the foot pointing directions; and
determining the user foot gesture is detected at each sampling time based on the checking result.

8. The method according to claim 7, further including:
using additional feature information, including pressure measurements at the four designed sole areas, in conjunction with the detected user touch detection outcome and foot pointing directions to support detection of new types of user foot gestures and to improve foot gesture detection performance.

9. The method according to claim 7, wherein:
the user foot gestures include Left foot taps, Right foot taps, one foot hops, jump and four types of foot wiggling movements.

10. The method according to claim 1, wherein:
the obtained relationship between the compass sensor's reference coordinate system and a corresponding foot pointing direction is predetermined.

11. The method according to claim 2, wherein:
pressure measurements are used to provide additional feature information for foot gesture detections, which allows further differentiation among a same type of foot gestures including a differentiation of small jumps and big jumps.

12. A method for using an improved compass-sensor embedded footwear system comprising:
at a data sampling time, obtaining pressure measurements from pressure sensors embedded in a left footwear and/or a right footwear;
based on the pressure measurements, determining sole area touch detection results corresponding to ground touches made by areas on each footwear sole of the left footwear and/or the right footwear; and
obtaining compass measurements from a compass sensor in each of the left and/or right footwear to evaluate the corresponding left and/or right foot pointing directions in the local North-East coordinate system.

13. The method according to claim 12, further including:
using the sole area touch detection results from the left footwear and/or the right footwear to obtain a user touch detection outcome at each data sampling time; and
determining foot gestures based on current and history information of: the user touch detection outcomes, and the left and/or right foot pointing directions.

14. The method according to claim 12, wherein:
a pressure measurement from each pressure sensor is compared to a threshold level to determine if the corresponding sole area is in touch with the ground to provide a sole area touch detection result.

15. The method according to claim 12, wherein:
evaluating the left and/or right foot pointing directions in the local North-East coordinate system includes:
obtaining compass measurements from a compass sensor in each of the left and/or right footwear;
evaluating an angle from a North direction of the local North-East coordinate system to an axis of the compass sensor's reference coordinate system with the compass measurements;
obtaining a relationship between the compass sensor's reference coordinate system and a corresponding foot pointing direction based on the compass-sensor embedded footwear system; and
based on the obtained relationship and the angle from the compass measurements, evaluating the left and/or right foot pointing directions in the local North-East coordinate system.

16. The method according to claim 12, further including:
using measurements from an accelerometer, a gyro sensor and a compass sensor in each of the left and/or right footwears to derive the left and/or right foot pointing directions in the local North-East coordinate system.

17. The method according to claim 12, further including:
sending information including the sole area touch detection results, the foot pointing directions from the left footwear and/or the right footwear, and/or the pressure measurements to an external device for further processing and controls.

* * * * *